(12) United States Patent
Müller et al.

(10) Patent No.: US 7,674,852 B2
(45) Date of Patent: Mar. 9, 2010

(54) POLYVINYL ALCOHOL GELS, ESPECIALLY IN SITU GELLING GELS

(75) Inventors: Rolf Müller, Zürich (CH); Federico Innerebner, Zürich (CH)

(73) Assignee: Innogel AG, Huenenberg (CH)

( * ) Notice: Subject to any disclaimer, the term of this patent is extended or adjusted under 35 U.S.C. 154(b) by 260 days.

(21) Appl. No.: 11/574,310

(22) PCT Filed: Aug. 25, 2005

(86) PCT No.: PCT/CH2005/000497

§ 371 (c)(1),
(2), (4) Date: Feb. 26, 2007

(87) PCT Pub. No.: WO2006/021122

PCT Pub. Date: Mar. 2, 2006

(65) Prior Publication Data
US 2007/0213453 A1    Sep. 13, 2007

(30) Foreign Application Priority Data

Aug. 25, 2004 (DE) ................. 10 2004 041 368
Oct. 14, 2004 (DE) ................. 10 2004 050 254

(51) Int. Cl.
*A61F 2/44* (2006.01)
*C08F 16/06* (2006.01)
*C08L 29/04* (2006.01)

(52) U.S. Cl. ............ 524/503; 524/27; 524/35; 524/47; 524/48; 524/52; 524/55; 524/500; 524/56; 525/56; 525/57; 525/58; 623/17.12; 623/17.16

(58) Field of Classification Search ................ 524/27, 524/32, 35, 47, 48, 52, 55, 56, 500, 503; 525/56, 57, 58; 623/17.12, 17.16
See application file for complete search history.

(56) References Cited

U.S. PATENT DOCUMENTS

| 4,734,097 A * | 3/1988 | Tanabe et al. ................ 424/423 |
| 5,190,533 A * | 3/1993 | Blackburn ................... 604/367 |
| 2001/0029399 A1 | 10/2001 | Ku |
| 2002/0034547 A1 | 3/2002 | Pennings et al. |

FOREIGN PATENT DOCUMENTS

| JP | 57-190072 | 11/1982 |
| WO | 2004098756 A2 | 11/2004 |
| WO | 2006021122 A3 | 3/2006 |

* cited by examiner

*Primary Examiner*—David Wu
*Assistant Examiner*—Marie Reddick
(74) *Attorney, Agent, or Firm*—K&L Gates LLP

(57) ABSTRACT

The invention relates to polyvinlyl alcohol gels which are suitable for use in the organism and which are formed at the site of application (in situ) from a viscous liquid by partial crystallization and network formation.

15 Claims, 1 Drawing Sheet

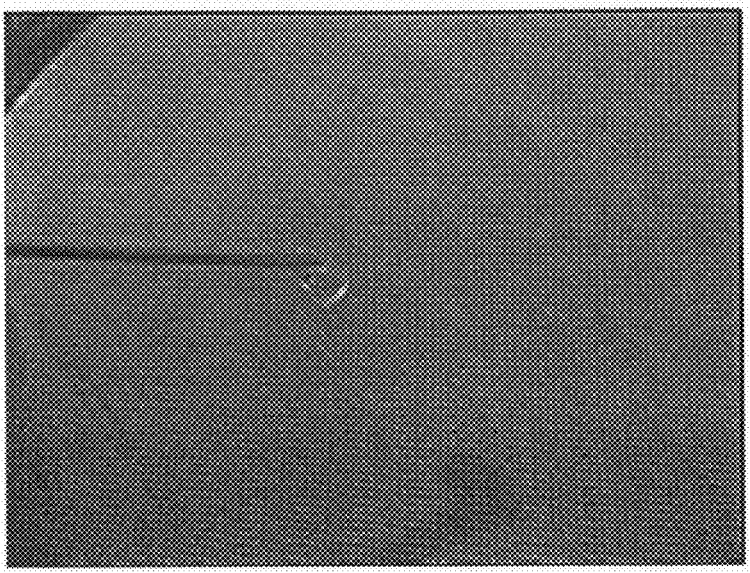
Fig. 1: In situ, solvatable PVA mixture as it exits an injection needle with a length of 5 cm and an inner diameter of 1 mm. Clear gel formation could be observed after about 3 min.
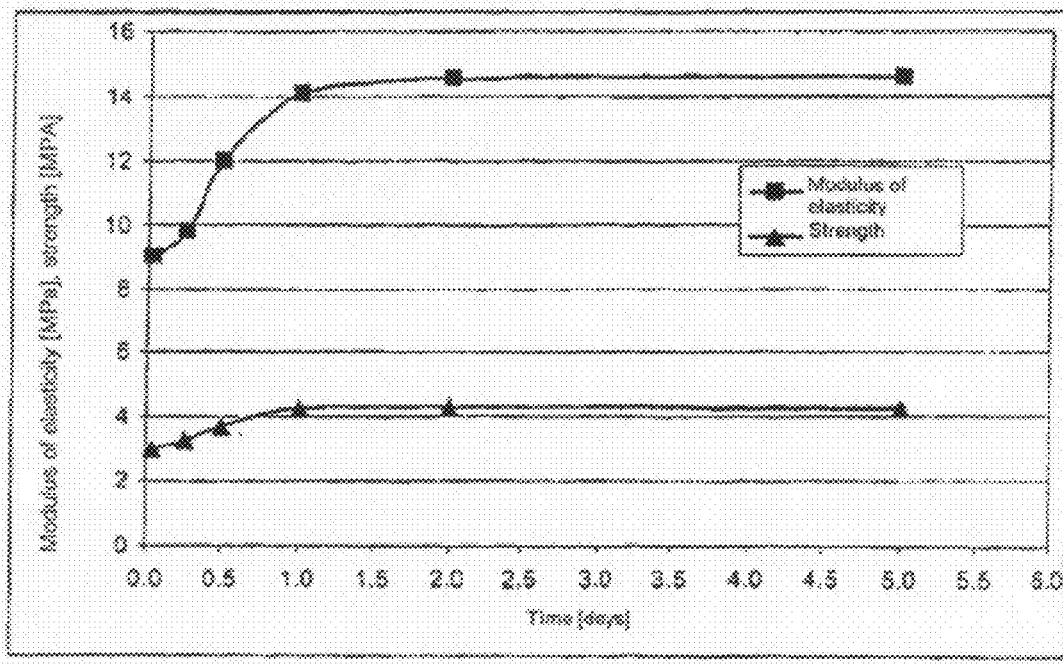
Fig. 2: Curing of in situ PVAG at 40°C. 62% of the modulus of elasticity and 71% of the strength had already been achieved after 1 h. The gel had practically completely cured after one day.

POLYVINYL ALCOHOL GELS, ESPECIALLY IN SITU GELLING GELS

BACKGROUND OF THE INVENTION

This invention relates to polyvinyl alcohol gels, in particular hydrogels, which are suitable for use in the organism, and formed at the site of application (in situ) out of a viscous liquid via partial crystallization and network formation.

Polyvinyl alcohol (PVA), which can be obtained via the hydrolysis of polyvinyl acetate, for example, is almost completely biodegradable, and readily water-soluble at elevated temperature. PVA-based hydrogels can be fabricated with the consistency of biological tissue and cartilage, and exhibit outstanding stability and biocompatibility in the living organism, which stems from the high water content of these gels on the one hand, and lies in the macromolecule itself on the other, which the organism perceives similarly to water due to the numerous hydroxyl groups. For this reason, PVA gels (PVAG) are all but predestined for applications in the living organism, in particular PVAG, which can be manufactured without cross-linking, radiation curing, and the assistance of problematical chemicals.

In the previous methods for manufacturing such PVAG, a solution of PVA is fabricated in a first step at elevated temperatures, e.g., 120° C., which can be cooled to room temperature and poured into a mold. Various methods are subsequently used for gel formation, wherein the PVA solution is frozen at least once, and then thawed again (freeze/thaw). Typically, the solvent is water, the PVA solutions have a concentration Cp of PVA ranging from 5 to 15%, and are cooled at rates of about 0.1° C./min to temperatures of roughly −15 to −30° C., left standing at this temperature for about 1 to 24 hours, and then thawed again at about 0.1 ° C./min. After such a cycle, the PVAG are opaque and very soft. They can already be damaged on contact, the strength sm of a PVAG with Cp=15% measures around 0.04 MPa, and the modulus of elasticity E measures around 0.01 MPa. The mechanical properties are continuously improved by repeating the freeze/thaw treatment, wherein the strength sm measures around 1 MPa, and the modulus of elasticity measures around 0.1 MPa after 10 cycles. Additional cycles further improve the mechanical properties to only a slight extent. These PVAG are copiously described in prior art, e.g., by F. Yokoyama et al in Colloid & Polymer Science (1986), 264, pp. 595-601.

U.S. Pat. No. 4,734,097 describes a modified method, in which only one freeze/thaw cycle is used proceeding from an aqueous PVA solution, e.g., with a Cp=8% in Example 3, and the PVA-water mixture is dehydrated in a frozen state under a vacuum for 10 hours to a concentration Cp of 42%. After thawing, a white opaque gel with a strength sm of 0.5 MPa was obtained, and proposed for use in the human body as artificial tissue. Patents applications were submitted for PVAG manufactured with this method for a plurality of applications, e.g., for artificial organs and membranes in EP 0107055 (artificial organs or membranes for medical use), as dermal gels in EP 0095892 (wound-covering materials), for use as a cooling medium in EP 0070986 (gel for use as cooling medium) as an isolation gel for low temperatures in JP 57190072, as a phantom for NMR diagnosis in GB 2209401 (phantoms for NMR diagnosis), or as a golf ball filling in GB 2182571 (golf ball cores).

U.S. Pat. No. 6,231,605 describes another modified method, in which three freeze/thaw cycles at −20° C. are first executed proceeding from an aqueous PVA solution, e.g., with a Cp=15% in Example 1, after which the obtained gel is placed in water, and swelled in this way. While the gel was transparent in this state, it was so weak that it could not sustain its shape outside of water. The swelled gel subsequently underwent two more freeze/thaw treatments, and then yielded an opaque elastic gel with a modulus of elasticity of roughly 0.4 MPa. Such gels were also proposed as tissue replacement in the human body, e.g., for heart valves, vessels, tendons, cartilage, meniscus, and urethras.

In another modified method in U.S. Pat. No. 4,663,358, the PVA solution is fabricated using mixtures of water and organic solvents, in particular DMSO, and then frozen at −20° C. The obtained gel is subsequently stored in water to largely extract the DMSO, dried in the atmosphere and then dried under a vacuum to extract the remaining DMSO. After swelled in water, the samples yielded PVAG exhibiting a transparency of up to 99% and strengths of up to 5.6 MPa. Such transparent PVAG were proposed for applications in the area of biomedicine and for the food industry.

As mentioned, the cited methods for manufacturing biocompatible PVAG shared in common that the process began with a pourable solution, and at least one freeze/thaw cycle was used. The known methods are obviously not suitable for in situ solvating, during which the PVAG is formed inside the organism at the application site. These applications require that:

1. The PVA-H2O mixture exhibit a sufficiently low viscosity, so that the mixture can be introduced to the application site in the body through a cannula, for example, and
2. Gel formation takes place from the PVA-H2O mixture at body temperature.

Since no methods were initially found that could satisfy these conditions, PVAG were manufactured for biomedical applications outside the body and then implanted. However, the advantages of PVAG formed in situ could not be utilized, e.g., minimally invasive surgical techniques. Methods for fabricating in situ solvating PVAG are based on the chemical cross-linking of injectable PVA solutions. Such methods are described in US 2004 166088 A1, U.S. Pat. No. 6,602,291 and WO 2004 07069296 A1. The disadvantage to these methods is that cross-linking via chemical reactions generates heat, which can damage the surrounding tissue, and that the chemical reaction yields various undesirable byproducts that represent a difficultly calculable risk.

US 2004 0171740 A1 and US 2004 0092653 A1 describe another approach toward in situ solvating PVA solutions. Gel formation here takes place physically, by forming networks via partial crystallization. While this is made possible by elevating the Flory interaction parameters via the addition of salts, the salts must be used in a high concentration (1.5 to 6 molar). As a result, this method also involves the introduction of substances into the organism that are not desirable, and can lead to complications.

This invention describes a solution to the described problems, wherein a solution exhibiting injectable polyvinyl alcohol and water is hardened at body temperature via partial crystallization and network formation into a gel with astounding mechanical properties. No substances other than PVA and water are needed to ensure that this happens. The invention describes the simplest possible case in this regard.

SUMMARY OF THE INVENTION

The invention describes a mixture of PVA and water, which forms a network at body temperature, in particular in the living organism (in situ), via partial crystallization. The mixture is low-viscous enough so that it can be brought to the application site in a minimally invasive manner, e.g., via a cannula. The gel formation kinetics along with the mechanical properties of the hardened gel can be set within broad limits, wherein a noticeable to distinct gel can be achieved after several minutes. The viscosity of the mixture, solvating kinetics and end properties can be varied within broad limits and tailored to specific requirements. Such in situ solvating PVA mixtures are suitable as a replacement for biological tissue and cartilage, and can be used to repair defective intervertebral disks (hernias).

Type of Used PVA

While preferably fully hydrolyzed PVA with the highest polymerization degrees DP of up to about 18,000 were preferably used for PVAG with a high strength and modulus of elasticity, this invention takes a partially different approach A first, preferably fully hydrolyzed PVA1 with a high number average polymerization degree DPn is used on the one hand, while this PVA1 is also combined with a preferably fully hydrolyzed PVA2 with average and especially low DPn ranging from about 1000 to 40. It is immediately clear that mixing PVA1 and PVA2 lowers the viscosity of the solution, and makes it possible to process higher concentrations Cp via solution procedures. A PVA with DPn=180, for example, has a viscosity of only 100 mPas at Cp=20% and room temperature, wherein the limiting viscosity of about 30,000 mPas is reached only at a Cp of about 60% at room temperature. At 100° C., Cp can even reach as high as about 70%.

One would first expect the percentage of PVA2 to reduce the mechanical properties of the resulting PVAG, i.e., thereby at least partially eliminating the advantage of a higher solution concentration. Surprisingly, however, the opposite effect was in fact discovered. Replacing a percentage of PVA1 by PVA2 at a constant Cp yields PVAG with a higher modulus of elasticity, so that the presumed disadvantage actually becomes an advantage, adding to the obvious advantage of a higher solution concentration Cp. This tendency remains valid up to a high degree of PVA1 substitution by PVA2. Solid elastic gels with a high extensibility can also still be obtained for PVA1:PVA2=5:95, while brittle gels with a low extensibility result during the use of just PVA2. Therefore, the effect of PVA2 can be explained by the fact that short-chain PVA can crystallize very readily, i.e., rapidly, completely and, in particular, even at temperatures >0° C., thereby increasing the crystalline percentage of PVAG. The improved crystallizability of PVA2 relative to PVA1 owes at least in part to the varying crystallization entropy.

In addition, PVA1 and PVA2 undergo heterocrystallization, i.e., the crystallites that form the linking points in the network constituting the gel exhibit both PVA1 and PVA2 macromolecules, wherein the shorter-chain PVA2 macromolecules induce the crystallization of segments of PVA1 macromolecules into heterocrystallites. As a result, higher overall network densities are achieved, i.e., narrow-meshed networks, and hence a higher modulus of elasticity for the resulting PVAG.

The use of PVA3, the long chain branches of which have a DP of >25, makes it possible to further improve the mechanical properties of PVAG, in particular if PVA3 is combined with PVA2 and/or PVA1. Incorporating the various side chains into different crystallites via heterocrystallization yields additional linking points of the network, wherein these linking points are then covalent in nature.

While pourable concentrations Cp ranging from 5 to at most 30% (depending on the PVA DP) were commonplace before, a range of 30 to about 90% has now become accessible, wherein even lower Cp concentrations than 30% are possible with this method, as particularly the case at very high PVA1 DPn. By using a percentage of PVA2 that contributes only little to the viscosity, the viscosity can be kept low, even at high concentrations Cp. As Cp increases, PVA-water mixtures increasingly exhibit an entirely different behavior in terms of gel formation in comparison to gel formation from a low-concentrated solution. While water must be removed from the PVA in the freeze/thaw process via the freezing procedure (formation of phases of frozen ice in addition to phases with very high Cp or low water content), which induces crystallization, Cp is high from the very outset in the new method, and freeze/thaw cycles are no longer absolutely mandatory. Gel or network formation via crystallization is also possible at higher temperatures. For example, at a Cp of around 40%, gel formation at room temperature is just as effective as when using freeze/thaw cycles. The higher the Cp and percentage of PVA2, the higher the temperature at which gel formation begins, so that even temperatures exceeding room temperature can be used, in particular at body temperature. In the simplest case, a PVA-water mixture can simply be stored at body temperature after molding, during which gel formation runs its course. The strength of the obtained PVAG increases steadily with the Cp, wherein values of 25 MPa and a modulus of elasticity of 30 MPa can be set, and complete transparency can also be obtained. If PVAG manufactured in this way are placed in water, swelling takes place, causing the Cp and mechanical properties to taper off somewhat. The swelling degree is here determined significantly by the set network density, and can also be specifically set via their parameters, in particular minimized.

BRIEF DESCRIPTION OF THE DRAWINGS

A detailed description of preferred embodiments of the invention follows, with reference to the attached drawings, wherein:

FIG. 1 shows expulsion of PVA solution through the injection needle; and

FIG. 2 presents the curing process as a function of time based on the modulus of elasticity and strength.

DETAILED DESCRIPTION

PVA1, PVA2, PVA3

To select the suitable PVA types, a distinction is made between three groups of parameters, the parameters affecting PVA regularity, such as hydrolysis degree H, content G of 1,2-glycol, tacticity, and percentage of short-chain branches, the parameters for molecular weight distribution, such as DPn (numerical average), DPw (weight average), as well as the parameters for macromolecule topology, such as branching degrees of long chains and length of these long or side chains.

With respect to the first group of parameters, the same requirements are placed on PVA1, PVA2 and PVA3 that enable the best possible crystallizability of PVA and a high crystallite stability. As a result, percentage deviations from the ideal structure $[-CH_2-CHOH-]_n$ are to be held as low as possible.

The hydrolysis degree H in mol. % of PVA1, PVA2 and PVA3 is >98, preferably >99, more preferably >99.2, and even more preferably >99.4. In a particularly advantageous embodiment, especially for PVA2, H>99.85, preferably >99.9, more preferably >99.95, most preferably >99.98. At these high hydrolysis degrees, just a slight increase has a profoundly distinct effect on the end properties of the gel.

A content G of 1,2-glycol in mol. % of <3 is advantageous, preferably <1, more preferably <0.5, and most preferably <0.2.

The number of short-chain branches per monomer unit advantageously measures $<10^{-2}$, preferably $<10^{-3}$, more preferably $<10^{-4}$, and most preferably $<10^{-6}$.

Further disruptions to regularity, such as carbonyl groups in the chain, are also undesirable, but their percentage in conventional PVA is negligible at a typical <0.02 mol. %.

With respect to tacticity, an atactic conformation is preferred to an isotactic conformation, with a syndiotactic conformation or as high a percentage of syndiotactic diads being most preferred. The tacticity of PVA is established by the type of monomer, so that the precursor polymer that later yields the PVA is polymerized, as well as by the reaction conditions during this polymerization, wherein the syndiotactic percentage increases as the temperature decreases during polymerization.

If the precursor polymer is polymerized out of vinyl acetate derivatives of the type $CH_2=CHOCOR$, wherein R can be H, $CH_3$, $C_3H_7$, $C_4H_9$, $CClH_2$, $CCl_3$, $CF_3C_4H_5F_4$, $C_6H_7F_6$ or $C_6H_5$, the percentage of syndiotactic diads increases with the volume of group R (while the 1,2-glyocol content advantageously decreases), and the tacticity obtained in the precursor polymer is retained during subsequent hydrolysis to the PVA. Therefore, the monomers preferred for polymerizing the precursor polymer include vinyl acetate, vinyl chloroacetate, vinyl dichloroacetate, vinyl bromoacetate, in particular vinyl trifluoroacetate.

If the precursor polymer is manufactured out of aliphatic vinyl acid esters, high percentages of syndiotactic diads are also obtained, while the resulting PVA also exhibit very low 1,2-glycol contents. Examples include vinyl formate, vinyl propionate, vinyl butyrate, and vinyl pivalate. Vinyl pivalate makes it possible to achieve very high molecular weights as well.

Fully hydrolyzed PVA obtained from polyvinyl acetate are also soluble at high crystallization degrees in water at 100° C., while fully hydrolyzed PVA whose precursor polymers were fabricated out of vinyl acetate derivatives with voluminous R group (e.g., vinyl trifluoroacetate) or aliphatic vinyl acid esters (e.g., vinyl fromate, vinyl pivalate) can be obtained in insoluble form even at 100° C. owing to the low 1,2-glycol content and the high percentage of syndiotactic diads. This highlights the importance of these parameters for the crystallizability and stability of the crystallites. Such PVA are hence especially well suited for the present invention.

Different requirements are placed on PVA1, PVA2 and PVA3 relative to molecular weight distribution. The literate typically cites a lower limit for average polymerization degree DP of 1000 to 15000 for previous PVAG based on only a single PVA, while the type of average value (DPn, DPw, DPv) is most often not specified. The polydispersity P=DPw/DPn of PVA obtained from polyvinyl acetate via saponification ranges from about 2 to 2.5, thereby enabling a conversion of these average values, and interpretation. Friable and brittle PVAG were obtained according to previous methods at DPn of around 500. This is explained by the fact that the macromolecules are not long enough to form effective links between crystallites. As a result, the crystallites can easily slide by each other, yielding virtually no strength. As the DPn decreases, this friable consistency increases further. One precondition for effective compounds is that at least two segments of a macromolecule be incorporated into at least two crystallites. As DPn increases, so too do the number of crystallites involving the participation of various segments of a PVA macromolecule, yielding mechanically more stable and increasingly elastic networks, making the highest possible DP advantageous for previous PVAG. The fact that only friable and brittle PVAG are obtained at low DP may have been a reason why low DP's were not taken into account for PVAG.

With respect to PVA1 and PVA3, the present invention uses DPn>1000, preferably >1500, more preferably >2000, most preferably >3000. Prior art sets the upper limit on the manufacture of highest molecular PVA, wherein PVA with a DP of about 18,000 can currently be manufactured.

With respect to PVA2, PVA with comparatively low DP are used, so as to reduce the viscosity of the solutions and melts on the one hand, and to enable crystallization even at temperatures >0° C. and high crystallization rates, crystallization degrees and high network densities on the other. PVA2 is used in this invention with DPn's ranging from about 40 to 1000, preferably 50 to 900, more preferably 70 to 800, and most preferably 75 to 700. The lower limit is defined by the stability of the crystallites formed by the PVA2 (wherein PVA1 and PVA3 segments are incorporated via heterocrystallization). The lamellar thickness of these crystallites at low DP is directly proportional to the DP, and the stability relative to temperature and solvent (water) increases with lamellar thickness. At high DP, the lamellar thickness most often decreases again, since the macromolecules then no longer crystallize in the fully stretched conformation, but rather a retraction preferably takes place, resulting in a lower smaller lamellar thickness. As a result, the selection of suitable DP for PVA2 at high hydrolysis degrees can also yield a positive effect with respect to the stability of crystallites, which is especially significant for in vivo applications for PVAG. The optimal DP range here measures about 75 to 700.

In terms of topology, PVA are predominantly linear, wherein long-chain branches are encountered for conventional PVA's rarely, if at all. Nearly complete or complete linearity is preferred for short-chain PVA2, wherein this condition is virtually always satisfied, wherein long-chain PVA1 do not necessarily have to be as linear as possible, wherein a percentage of long-chain branches in PVA1 can even be advantageous if the length of these side chains has a DP>40. By contrast, a notable percentage of long-chain branches is the decisive feature in terms of the functionality of PVA3, wherein the same requirements as for the DP of PVA2 apply relative to the polymerization degrees DP for these long or side chains. Therefore, it is possible to incorporate the various side chains of a macromolecule PVA3 into various crystallites (together with PVA1 and/or PVA2), resulting in an increased cross-linking of these crystallites, i.e., greater network densities. PVA3 type PVA's are currently not commercially available. However, we know for PVA obtained from polyvinyl benzoate that long-chain branches can be obtained under suitable reaction conditions during the polymerization of vinyl benzoate. Another way of manufacturing PVA3 involves grafting PVA2 type PVA onto PVA1 type PVA, wherein the number and length of the side chains can be set.

Mixtures

In an advantageous embodiment, the percentage of PVA1 relative to PVA1+PVA2 in %w/w ranges from 3-60, preferably 5-50, more preferably 7-40, and most preferably 8-35. Selecting the percentage of PVA1 sets the viscosity of the solution on the one hand, wherein the viscosity increases with the percentage of PVA1. On the other hand, increasing the percentage of PVA2 lowers the viscosity and facilitates crystallization, i.e., it can take place at higher temperatures, and at a faster rate. The percentage of PVA1 also depends on what type of PVA1 is used. For example, the percentage of PVA1 is set low, e.g., to 8%, at high polymerization degrees for PVA1.

A high percentage of PVA2 relative to PVA1+PVA2 is advantageous for adjusting a high modulus of elasticity, wherein very high expansions are astoundingly still obtained.

The percentage of PVA3 relative to PVA1+PVA2+PVA in % w/w ranges from 1 to 80, preferably from 2 to 60, and most preferably 3 to 50.

The percentage of PVA relative to PVA and swelling means in %w/w ranges from 5 to 80, preferably from 10 to 70, more preferably from 15 to 60, and most preferably from 20 to 50.

IN an advantageous embodiment, the dynamic viscosity at 70° C. for the mixture in MPas measures <30,000, preferably <20,000, more preferably <15,000, and most preferably <10,000.

Preparation and Gel Formation

In order to manufacture PVAG according to the invention, the components PVA1, PVA2 and, if necessary, PVA3 are transferred into an aqueous solution. A Ringer's solution is preferably used for the dissolution process. The components can here be dissolved separately or together, and the known standard methods can be used for manufacturing the solution. It is important that the components be thoroughly mixed, for which various known mixing methods for viscous solutions can be used. The solvating capability under in situ conditions (around 37° C., in the body), solvating kinetics and end properties of the gel are set by the type of used components, their ratio, and the water content.

Properties

The gels according to the invention are characterized by the simple processability, rapid gel formation, good mechanical properties and high stability. The ability to purposefully influence various properties and obtain specific property combinations is rooted in the fact that a significant new degree of freedom is made available by the short-chain PVA2 and its parameters (hydrolysis degree, DPn, minimal DP, cleaning) relative to other solutions.

In an advantageous embodiment, at least 10% of the modulus of elasticity and/or the strength of the solidified state is reached after one hour, preferably at least 25%, more preferably at least 40%, and most preferably at least 50%. As the percentage of PVA2 increases, the gel formation rate rises, as with the hydrolysis rate of PVA1, and in particular of PVA2.

In an advantageous embodiment, the gels have a modulus of elasticity and/or a strength in MPa in the tensile mode and/or compression mode measuring 0.1 to 25, preferably 0.25 to 25, more preferably 0.5 to 25, and most preferably 0.75 to 25. The effect of the different parameters on the mechanical properties can be gleaned from Table 1.

Also of great importance is the stability of the gels during application. Classic freeze/thaw PVA gels have a weakness with respect to stability. Since gel formation takes place at very much lower temperatures (<<0° C.) than the temperature of use (37° C.), a percentage of the crystallites are not stable at this temperature of use. They break down again, and macromolecules go into solution. Since the temperature of use is identical to the gel formation temperature in the gels according to the invention, this loss of polymer that weakens the gel does not take place. In addition, the lowest possible loss of polymer is advantageous for in vivo applications. On the other hand, polymers can still go into solution if they are too short to form stable crystallites, or if the hydrolysis degree is too low, or if other deviations from the regular structure take place. Such unsuitable macromolecules can be eliminated by dissolving the polymers beforehand and precipitating them under suitable conditions, during which the unsuitable macromolecules remain in the solution. Another approach would be to post-hydrolyze the polymers as completely as possible, and filter out excessively short macromolecules, e.g., via dialysis. The methods employed for this purpose are described below (examples 2-12, analyses), and the impact on polymer loss after 14 days (V14) in distilled water can be gleaned from table 1. In a preferred embodiment, the polymerization degree for the smallest macromolecules of the molecular weight distribution of PVA1 and PVA2 measures >40, preferably >50, more preferably >60, and most preferably >70.

In a advantageous embodiment, V14 in % measures <7, preferably <4 more preferably <3, and most preferably <2.

In general, the water content of the formed gels is increased if they are placed in water (swelling). However, the same measures that lead to a reduced in V14 also clearly decrease the swelling degree, so that the water content after swelling is only slightly greater than before. As a result, gels with outstanding mechanical properties can also be obtained. The swelling degree can be further minimized by having gel formation take place in a Ringer's solution, and execute the swelling process in a Ringer's solution. As a result, the conditions are also very close to those in the organism where the gel is used.

Swelling Agents

Swelling agents here refers to swelling agents in a narrower sense, as well as to solvents. The most important swelling agent is water, and water is in most cases used as the sole swelling agent, or in mixtures with other swelling agent, wherein the solvents and swelling agents and mixtures thereof described in prior art are also possible, however, such as DMSO, dimethyl formamide, acetamide or polyols like glycerin, erythritol, xylitol, sorbitol, mannitol, galactitol, tagatose, lactitol, maltitol, maltulose, isomalt, methylene glycol, ethylene glycol, diethylene glycol, triethylene glycol, propylene glycol, butane diol, pentane diol, and hexane triol. The swelling agent can also exhibit a percentage of salt (saline solution, Ringer's solution).

Other Polymers

In addition to PVA, the PVAG can also contain other polymers to modify properties and for specific applications, e.g., synthetic polymers like polycarbonates, polyacrylates and polymethacrylates, polyethylene glycols, polyethylene oxides, polyvinyl pyrrolidones, polycaprolactones or polymers of a natural origin, such as hydrocolloids and polysaccharides, in particular starch and starch derivatives.

Additives

Additives refers to simple fillers and functional fillers or active agents.

Applications

The fact that the PVAG according to the invention can be obtained with a broad range of mechanical properties enables an entire series of applications. On the one hand, previous PVA gels can be advantageously replaced in all applications, since the new gels are much easier to manufacture (pourability, gel formation temperature >0° C., stability), and exhibit at least as good mechanical properties. On the other hand, the new gels are opening up extremely interesting applications in the area of biomedicine (e.g., tissue and scaffold engineering), and in particular in orthopedics, especially as in situ gels. Tissues, gels, cartilage, in particular tendons, ligaments, joint surfaces, menisci, nerve sheaths, urethras, heart valves, gel bodies of the intervertebral discs (nucleus) can be replaced or repaired. In the area of the intervertebral discs, the following specific applications are possible in particular: total disc replacement, nucleoplasty, facet replacement, segment replacement, vertebroplasty, kyphoplasty, lordoplasty. Other applications involve cosmetic or plastic surgery, where the gels represent an alternative to silicone implants.

EXAMPLES

Example 1

PVA1: 99.4% hydrolyzed, DPn=2200, PVA2: 98.5% hydrolyzed, DPn=180. 10 g of PVA1 was dissolved with 100 ml of H2O in a flask while blending with a magnetic agitator at 1000° C. for 30 mm 35 g of this homogenous solution were transferred into a Brabender kneader. The kneader temperature measured 90° C., and the speed was set to 180 RPM. 30 g of PVA2 in the form of powder was metered into the solution in the kneading chamber. A homogenous mixture was obtained after 4 min. of mixing. The water content of this mixture measured about 49% (water relative to PVA and water), and the percentage of PVA1 relative to PVA1 and PVA2 measured about 9.6%. 5 ml of the mixture were siphoned into a syringe that had previously been heated at 40° C. After 3 min., the PVA solution was expelled through an injection needle IN1 with a length of 5 cm and an inner diameter of 1 mm onto a Petrie dish heated to 40° C. The viscosity was low enough that the solution could be expelled by hand through the injection needle with little force. After about 3 min., distinct gel formation was noted. The rest of the mixture was used to manufacture a 0.5 mm thick film, with which tensile tests and stability analyses were performed.

FIG. 1 shows the expulsion of PVA solution through the injection needle. FIG. 2 presents the curing process as a function of time based on the modulus of elasticity and strength. Breaking elongation only varied slightly with curing time, measuring roughly 300%. The modulus of elasticity in the tensile test measured 14.5 MPa after curing, while the strength was around 4.2 MPa. The stability analysis revealed a polymer loss V14 of 6.8%.

Examples 2-12

A procedure comparable to the one in Example 1 was used in Examples 2-12. The percentage of PVA1, water content of the mixture and used PVA types were varied. The corresponding data and properties of the obtained gels are shown in Table 1. In examples 4-12, the solution of PVA was also manufactured with a Ringer's solution instead of pure water. The hydrolysis degrees H>99.4 mol. % of PVA1 and the hydrolysis degree H>98.5 mol. % of PVA2 were obtained via posthydrolyzation. In Example 5, the PVA2 was cleaned by precipitating a 20% solution at 5° C., wherein the better crystallizing macromolecules were selectively precipitated. The stability analysis consequently revealed a distinctly improved polymer loss V14 of just 1.2%. As shown by the results on Table 1, distinctly improved stability values V14 could also be obtained by increasing the hydrolysis degree of PVA1 and PVA2. Further, very good mechanical properties could still be obtained even at the highest water contents.

Examples 10 and 11 are well suited for restoring defective intravertebral discs. With the annulus still intact, a gel strength in compression of 1-2 MPa and a modulus of elasticity in compression of about 0.5-2 MPa is here required, the gel volume measures roughly 5 ml, and the temperature of the injected PVA solution should lie below about 55° C., solvating should take place at 37° C., and the viscosity of the PVA solution should be low enough to enable its injection through a cannula with an inner diameter of roughly 2 mm. If the annulus is no longer intact (e.g., given a hernia), the required gel strength measures around 2-5 MPa, while the other conditions remain identical, except for the diameter of the cannula, which can be as high as 6 mm. Example 12 shows properties of the kind required for cartilage. The other examples show that higher values that required are also possible, i.e., a broader range of mechanical properties is accessible. The cited examples are optimized gels; of course, gels with a lower modulus of elasticity and strength can also be used.

Analyses

Hydrolysis degree H: Determination of the ester number pursuant to DIN 53401.

Polymerization degree: Determination of the limiting viscosity according to C. A. Finch (Polyvinyl Alcohol, Properties and Applications, 1973) and correlation of the obtained limiting viscosities with the limiting viscosities of polyvinyl standards with a known DPn.

Hydrolyzation: Saponification of polyvinyl alcohol, types Mowiol 3-98, 4-98, 6-98, 56-98 and 66-100 with NaOH at 25° C. at an initial pH of 12 according to C. A. Finch (Polyvinyl Alcohol, Properties and Applications, 1973). Increasing hydrolysis degrees were obtained by extending the reaction times, wherein the reaction was stopped by lowering the pH to 7. The reaction products were then precipitated with acetone (acetone:water=1:1), washed in water:acetone=2:1 in a Nutsch filter, dried and pulverized (impact mill), or (Tests 10-12) first dialyzed for 48 h after the reaction (molecular weight cut off=3500, Spectra/Por, Spectrum), then precipitated with acetone, dried and pulverized. The dialysis made it possible to separate out shorter polymer chains, which are unable to form any stable crystallites, thereby improving both the stability and mechanical properties.

Mechanical properties: The mechanical properties in the tensile mode and compression mode were tested with an Instron Tensile Tester 5542. The samples for the tensile tests were stamped out of pressed films 0.5 mm thick, and have a sample length of 13 mm and a width of 2 mm. The expansion rate measured 10 cm/min. The samples for the compression tests were stamped out of cast plates 0.5 cm thick as round objects 0.5 cm in diameter. The compression rate was about 0.5 cm/min. The obtained measured values represent the average of 5 individual measurements.

Stability analysis: Films 0.5 mm thick with a surface area of 1 cm2, a water content W0 and a weight M0 were stored for 14 days in excess water at room temperature. The films were then wiped with absorbent paper to remove surface water, weighed (weight M1), and measured for water content (W1). The mass loss in % after 14 days (V14) was then obtained as $100 (1-M1(1-W1)/(M0(1-W0)))$.

Injectability: Two types of injection needles were used: IN1 had an inner diameter of 1 mm and a length of 5 cm, IN2 had an inner diameter of 0.7 mm and a length of 7 cm. The injectability was assessed as positive if at least 2 g of PVA solution could be manually expelled at 40° C. for 1 min.

Viscosity: Dynamic viscosities were measured with a cone-plate viscometer US 200 from Paar Physica at 70 ° C.

TABLE 1

| | PVA1 | | PVA2 | | PVA1/ | | Properties | | | | | Sprayability | |
|---|---|---|---|---|---|---|---|---|---|---|---|---|---|
| | DPn | H | DPn | H | PVA | H2O | E | F | e | V14 | | | |
| Nr. | [ ] | [mol %] | [ ] | [%] | [%] | [%] | [MPa] | [MPa] | [%] | [%] | IN1 | IN2 |
| 1 | 2500 | 99.4 | 180 | 98.50 | 9.6 | 49 | 14.5 | 4.2 | 300 | 6.8 | yes | no |
| 2 | 2500 | 99.4 | 180 | 98.50 | 8.4 | 54 | 4.0 | 1.5 | 220 | 6.9 | yes | yes |
| 3 | 2500 | 99.4 | 180 | 99.60 | 9.6 | 50 | 18.1 | 9.4 | 450 | 3 | yes | no |
| 4 | 2500 | 99.4 | 180 | 99.90 | 9.6 | 50 | 20.4 | 14.5 | 490 | 2.2 | yes | no |
| 5 | 2500 | 99.4 | 180 | 99.90 | 9.6 | 50 | 21.0 | 14.4 | 510 | 1.2 | yes | yes |
| 6 | 2500 | 99.9 | 180 | 99.95 | 11 | 55 | 11.7 | 7.2 | 270 | 0.9 | yes | yes |
| 7 | 2500 | 99.9 | 300 | 99.95 | 11 | 55 | 14.1 | 8.0 | 320 | 0.8 | yes | no |
| 8 | 2500 | 99.9 | 180 | 99.95 | 17 | 60 | 9.9 | 7.1 | 280 | 0.9 | yes | yes |
| 9 | 2500 | 99.9 | 300 | 99.95 | 17 | 60 | 11.8 | 7.5 | 290 | 0.8 | yes | yes |
| 10 | 2500 | 99.9 | 180 | 99.97 | 30 | 71 | 1.5* | 2.7* | >80* | 0.7 | yes | yes |
| 11 | 2500 | 99.9 | 300 | 99.97 | 30 | 69 | 2.2* | 4.6* | >80* | 0.7 | yes | yes |
| 12 | 2500 | 99.9 | 600 | 99.97 | 30 | 65 | 7.1* | 10.5* | >80* | 0.6 | yes | yes |

DPn: Numerical average of polymerization degree;
H: Hydrolysis degree;
PVA: PVA1 + PVA2;
H2O: Water content of mixture
E: Modulus of elasticity;
F: Strength;
e: Breaking elongation/compression at break;
V14: Polymer loss in water after 14 days;
IN1: Injection needle with an inner diameter of 1 mm and length of 5 cm;
IN2: Injection needle with an inner diameter of 0.7 mm and length of 7 cm.
*Values for compression mode, other values for tensile mode.

The invention claimed is:

1. An injectable polyvinyl alcohol gel, characterized in that
   a) the gel comprises polyvinyl alcohol and water and is formed from a solution at 0 to 100° C.; and
   b) the gel comprises at least one polyvinyl alcohol PVA1, and at least one polyvinyl alcohol PVA2; and
   c) the polymerization degree DPn of PVA1 is >1000; and
   d) the polymerization degree DPn of PVA2 ranges from 50 to 1000; and
   e) the hydrolysis degree of PVA1 and PVA2 in mol. % is >98.

2. The injectable polyvinyl alcohol gel according to claim 1, characterized in that the hydrolysis degree of PVA2 in mol. % is >99.85.

3. The injectable polyvinyl alcohol gel according to claim 2, characterized in that the hydrolysis degree of PVA1 in mol. % is >99.85.

4. The injectable polyvinyl alcohol gel according to claim 1, characterized in that the smallest macromolecules of the molecular distributions of PVA1 and PVA2 have a polymerization degree of >40.

5. The injectable polyvinyl alcohol gel according to claim 1, characterized in that gel formation takes place in the body temperature range under in situ conditions.

6. The injectable polyvinyl alcohol gel according to claim 1, characterized in that the gel has a modulus of elasticity ranging from 0.1 to 25 MPa at room temperature in at least one of compression and in the tensile test.

7. The injectable polyvinyl alcohol gel according to claim 1, characterized in that the gel has at least 10% of at least one of the modulus of elasticity and the strength of the cured state after 1 h.

8. The injectable polyvinyl alcohol gel according to claim 1, characterized in that a film of 0.5 mm thickness swelled in distilled water at room temperature has a polymer loss in % after 14 days of <7.

9. The injectable polyvinyl alcohol gel according to claim 1, characterized in that the gel comprises at least one filler, and/or at least one additional polymer selected from the group consisting of polycarbonates, polyacrylates, polymethacrylates, polyethylene glycols, polyethylene oxide, polyvinyl pyrrolidone, polycaprolactone, hydrocolloids, and polysaccharides.

10. A method for carrying out a procedure in the area of biomedicine, tissue and scaffold engineering, orthopedics and plastic surgery wherein the procedure utilizes a previous gel, the method comprising the step of replacing the previous gel with an injectable polyvinyl alcohol gel according to claim 1.

11. A method for replacement and repair of intervertabral discs which utilizes the polyvinyl alcohol gel according to claim 1.

12. The injectable polyvinyl alcohol gel according to claim 1, characterized in that the hydrolysis degree of PVA2 in mol. % is >99.9.

13. The injectable polyvinyl alcohol gel according to claim 1, characterized in that the hydrolysis degree of PVA2 in mol. % is >99.95.

14. The injectable polyvinyl alcohol gel according to claim 1, characterized in that the hydrolysis degree of PVA2 in mol. % is >99.98.

15. The injectable polyvinyl alcohol gel according to claim 1, characterized in that a film of roughly 0.5 mm thickness swelled in distilled water at room temperature has a polymer loss in % after 14 days of <3.

* * * * *